United States Patent [19]

Ohtsuka et al.

[11] Patent Number: 4,705,836
[45] Date of Patent: Nov. 10, 1987

[54] POLYMERIZATION COMPOSITION CONTAINING VINYL BENZOIC ACID OR A DERIVATIVE THEREOF AND A VINYL COMPOUND

[75] Inventors: Masasuke Ohtsuka, Tokyo; Yoshinori Harada, Urawa; Shigeo Tokita, Chiba; Hideyo Maniwa, Kanagawa, all of Japan

[73] Assignee: Nippon Shiken Dental Co., Ltd., Tokyo, Japan

[21] Appl. No.: 794,140

[22] Filed: Nov. 1, 1985

[30] Foreign Application Priority Data

Jul. 8, 1985 [JP] Japan ................................ 60-148422

[51] Int. Cl.$^4$ .................. C08F 220/00; C08F 220/18; A61K 6/08
[52] U.S. Cl. ............................... 526/318.1; 106/35; 433/217.1; 433/228.1; 260/998.11; 523/118; 524/556; 524/562; 526/292.5; 526/293; 526/326
[58] Field of Search .................... 523/116, 117, 118; 433/228.1, 217.1; 260/998.11; 524/556, 562; 526/292.5, 293, 318.1, 326

[56] References Cited

U.S. PATENT DOCUMENTS

| | | | |
|---|---|---|---|
| 3,649,668 | 3/1972 | Dolinski et al. | 526/292.5 |
| 4,259,117 | 3/1981 | Yamauchi et al. | 526/278 |
| 4,364,924 | 12/1982 | Gander et al. | 526/240 |
| 4,415,631 | 11/1983 | Schutijser | 428/404 |
| 4,448,850 | 5/1984 | Upson et al. | 428/522 |
| 4,544,723 | 10/1985 | Upson et al. | 526/293 |

Primary Examiner—Paul Lieberman
Assistant Examiner—Linda D. Skaling
Attorney, Agent, or Firm—Stephen F. K. Yee

[57] ABSTRACT

Composites comprising
(A) general formula (I), compound of

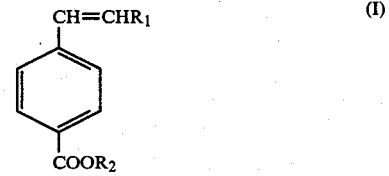

[in the formula, $R_1$ indicates either hydrogen or methyl group and $R_2$ indicates hydrogen, alkyl radical with carbon number 1–5 to be possibly substituted with halogen, alkyleneoxide group with carbon number 2–4 to be possibly substituted with halogen or —$(CH_2CH_2O)_nH$ group (n=integral number of 1–4) to be possibly substituted with either halogen or methyl group],
(B) vinyl compounds and/or silane compounds, and optionally
(C) free radical developing agent and/or light sensitizer have not only an excellent adhesiveness but anti-irritation and anti-harmfulness against tissue, pulp and the like, for teeth and dentin.

22 Claims, No Drawings

POLYMERIZATION COMPOSITION CONTAINING VINYL BENZOIC ACID OR A DERIVATIVE THEREOF AND A VINYL COMPOUND

FIELD OF THE INVENTION

The present invention relates to novel composites, particularly adhesive composites and adhesive anti-irritation and anti-harmfulness composites against tissue, pulp and the like.

BACKGROUND OF THE INVENTION

As a bonding agent for teeth, methylmethacrylate polymer and copolymer of vinyl compounds such as 2,2-bis [4-(2-hydroxy-3-methacryloxypropoxy) phenyl]-propane and triethylene glycol dimethacrylate have been used so far, and recently adhesive composites containing 4-methacryloxy-ethyl trimellitic acid anhydride have been prposed and used as a bonding agent for teeth. As the former requires a preliminary treatment of teeth with strong acid due to insufficient adhesive force for teeth, such treatment has a defect of dissolving the surface of teeth more than necessary and also the dental treatment is complicated. The latter exhibits adhesiveness as the result of self curing, but when redox-polymerization catalyst is used as a polymerization catalyst at normal temperature, aromatic tertiary amine which is primarily to be an accelerator in this catalyzer system and the acid anhydride group of 4-methacryloxyethyl trimellitic acid anhydride forms the charge-transfer complex. Consequently the polymerization catalyst cannot perform its original function and polymerization becomes impossible, so the polymerization catalyst at normal temperature used in this adhesion system was practically restricted to tri-n-butylboronoxygen complex. This tri-n-butylboron-oxygen complex has an advantage of offering a strong adhesiveness for a dentin, while it has many disadvantages from the standpoint of dental clinic, i. e. its polymerization reaction is so slow as to take more than ten minutes for final hardening according to circumstances and it is so unstable in the air that its handling is difficult, etc. And yet no anti-irritation and anti-harmfulness properties against tissue, pulp and the like, could be expected from these composites at all.

Irritation and harmfulness against tissue, pulp and the like, often occur in the following case: when the dentin covering the pulp becomes extremely thin due to the depth of cavity, or the affected part is highly sensitive as the result of damage or exposure of the pulp by removing early caries and forming cavity, or when the cavity is directly filled up with composite resin or an usual bonding agent is applied to the cavity before it is filled up with composite resin, though the cavity itself comparatively shallow just as to slightly reach the dentin.

When such cavity was repaired hitherto, a pulp cap was normally used to protect live pulp. When the pulp inflamed because composite resin was filled up without treatment to protect the pulp, the plugging was removed and capping was renewed for later refilling when the inflammation was not serious. However, in case of serious occasions such as purulent inflammation or decay, there was nothing for it but to devitalize the affected tooth by pulpectomy.

Recently an adhesive liner has been invented, which is effective when it is applied to the dentin to form a tunic for protecting teeth against the permeation of external stimulus. Polyacrylic derivative is considered to be the principal component of the adhesive liner, but as this component is as harmful as conventional stuffs when applied to a deep cavity near the pulp or an exposed pulp, it is essential to use the conventional cap together with the adhesive liner for such a symptom and its process is comparatively complex.

SUMMARY OF THE INVENTION

As the result of further study about composites which are adhesive and effective against tissue, pulp and the like, irritation and harmfulness in order to solve above mentioned problems with conventional bonding agents, the present inventors have found that those composites containing vinyl benzoic acid, vinyl compounds, free radical developing agent etc. are ones which serve the purpose previously mentioned and have come to accomplish this invention.

Namely, the present invention relates to the composites, comprising
(A) compounds of General formula (I),

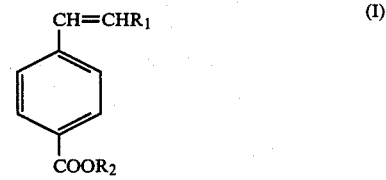

[in the formula, $R_1$ indicates either hydrogen or methyl group and $R_2$ indicates hydrogen, alkyl group with carbon number 1–5 to be possibly substituted with halogen, alkyleneoxide group with carbon number 2–4 to be possibly substituted with halogen, or —$(CH_2CH_2O)nH$ group (n=integral numbers of 1–4) to be possibly substituted with either halogen or methyl group],
(B) vinyl compounds and/or silane compounds, and optionally,
(C) free radical developing agents and/or light-sensitizer:

Further the present invention relates to the bonding agents consisting of these composites, particularly bonding agents for dental use and anti-irritation and anti-harmfulness compound against tissue, pulp and the like, consisting of these composites.

By using these composites as a structural component of a bonding agent, normal free radical developing agent can be used as a catalyst instead of tri-n-butylboron-oxygen complex which has been so far used in the mouth as a polymerization reaction at normal temperature in spite of slow polymerizing ability, and moreover the adhesive force of the present composites is excellent. The redoxpolymerization catalyst which is the combination of free radical developing agent, especially, peroxide with aromatic tertiary amine compounds has no adhesiveness for the dentin of tooth but it is advantageous from the clinical standpoint because the polymerizing speed can be controlled as occasion demands and the process is simple in addition to its inexpensiveness.

Though there are some examples of using this redox-polymerization catalyst for the composites of a bonding agent containing phosphate ester compound, in such a case, redox-catalyst consisting of peroxide such as benzoylperoxide and aromatic tertiary amine and other polymerization catalyst such as p-toluensulfonic acid are used jointly due to possible poor polymerization of composites. And yet there remained a problem that a considerable unpolymerized part exists especially at the surface of the bonding agent, where it contacted with the air. According to the present invention such non-polymerization part is little even if redox-catalyst alone is used.

Though 4-vinyl benzoic acid used in the present invention has ever been taken up as a substance for research of a series of bonding agents of dental use, it has not been practically used as an adhesive composite and/or a dental material.

In other words, there is an example that ethanol solution only containing 4-vinyl benzoic acid was used as a dental bonding agent. However, it is necessary to evaporate the ethanol, because if prompt hardening resin is applied to the ethanol solution without evaporating it, ethanol which does not take part in polymerization reaction remains at the adhesion surface, causes a poor adhesion and checks the polymerization reaction itself. However, if ethanol is evaporated, 4-vinyl benzoic acid remains on the solution applied surface as crystals. Therefore, if prompt hardening resin is applied to the adhesion surface, the polymerization (adhesion) reaction acts unevenly, which partially causes a poor adhesion and that much weakens the adhesive force, and it is of no practiced use.

Further, there is another example that chloroform solution of 4-vinyl benzoic acid-methyl methacrylate copolymer (VBA-MMA) was used as a bonding agent of dental use, but the chloroform used as solvent has to be evaporated same as above mentioned ethanol. In this case, however, it has a weak point of leaving crystals of the copolymer after evaporation and weakening its adhesive force and yet, since VBA-MMA copolymer is producted by previous polymerization of VBA and MMA in a closed tube filled with nitrogen, there is a possiblity that the reaction activity of the substance associated with adhesion, for example, reactivity of carboxyl group on tooth calcium or reactivity (copolymerization) with prompt hardening resin applied to the tooth calcium would be weaken to be resulted in poor adhesive force.

The present invention has realized for the first time practical use of adhesive composites, particularly for dental materials, which consist of the compound shown by the general formula (I) and vinyl compound as principal components and moreover for which free radical developing agents, for example, redox-polymerization catalyst can be used.

According to the present invention it is possible to apply a method that the adhesive composites containing 4-vinyl benzoic acids and vinyl compounds with high boiling point are diluted with solvent. In this case, even if the solvent was evapolated, 4-vinyl benzoic acids dissolved into vinyl compound would not develop into crystallization, and an even polymerization (adhesion) reaction occurs to result in an excellent adhesion. The substance associated with adhesion maintains the form of monomer to the end, and its reactivity of carboxyl group and reactivity (copolymerization) with prompt hardening resin is greater compared with copolymer. This is considered to be one of factors why an excellent result is obtained by the present invention.

Besides, irritation and harmfulness against tissue, pulp and the like, as previously described occur when the affected part is highly sensitive because the pulp is damaged and exposed as the result of formation of a cavity, or even if the cavity is shallow, when the cavity is directly filled with composite resin or when a conventional bonding agent is applied to the cavity before composite resin is filled. Regarding relationship between the filling of composite resin and irritation and harmfulness against tissue, pulp and the like, there are two opinions; one is that the factor is the permeation of bacteria through the interface of dental substance and resin and the other is that it is the harming action by unpolymerized monomer deluted from the composite resin filled up in a cavity. The former is mainly caused by the lack of the effectuality of brim blocking due to adhesion fault, and the latter is caused by the cellular toxicity of monomer itself including the bonding agent.

Recently, a bonding agent of dental use which shows a good adhesion has been invented and the problem of the brim blocking is being solved gradually but the cellular toxicity of monomer has not been solved. Therefore, a live pulp is normally protected by using a pulp cap such as paraformaldehyde group and calcium hydroxide before composite resin is filled up not only when a cavity is so deep as to reach the pulp or already exposed but when it is as shallow as to reach only dentin. When this treatment had been neglected, it was often found that the pulp got purulent or decayed at the worst. In such case, there was nothing for it but to devitalize the affected tooth by pulpectomy.

Also with regard to an adhesive liner recently invented, which is said to be effective when it is applied to the defective part of dentin to form a tunic for protecting the teeth against the permeation of external stimulants, it is essential to use the traditional cap together with the adhesive liner and to ge through the following process for its use.

Namely, when cavity is deep, the process in the known adhesive liner is,

1. Formation of cavity (dentin and enamel substances)
2. Capping the cavity
3. Mixing of liners (because of double solution type)
4. Application of the mixture to the defective part of dentin (formation of tunic)
5. Reelimination of enamel substance (elimination of tunic covering enamel substance)
6. Acid etching of enamel substance
7. Mixing of bonding agents (double solution type)
8. Application to the enamel substance
9. Mixing of composite resin
10. Filling of composite resin.

While, in case of the present composites, the process is,

1. Formation of cavity (dentin and enamel substances)
2. Acid etching (dentin and enamel substances)
3. Mixing of liners (in case of mono-solution type, this step is omitted)
4. Application (dentin and enamel substances)
5. Mixing of composite resin
6. Filling of composite resin.

Thus the handling process can be simplified compared with the former.

At the dental clinic a simpler treatment process is more desirable and the present composites which perform both capping and adhesion at one time are very valuable when a deep cavity which is inevitable to be capped in its nature is repaired with composite resin.

As compounds of (A) general formula (I) of the present invention the following are enumerated in case of $R_1$=H; materially, 4-vinyl benzoic acid, 4-vinyl benoic acid methyl ester, 4-vinyl benzoic acid chloromethyl ester, 4-vinyl benzoic acid bromomethyl ester, 4-vinyl benzoic acid ethyl ester, 4-vinyl benzoic acid 2-chloroethyl ester, 4-vinyl benzoic acid 2-bromoethyl ester, 4-vinyl benzoic acid n-propyl ester, 4-vinyl benzoic acid 3-chloropropyl ester, 4-vinyl benzoic acid 3-bromopropyl ester, 4-vinyl benzoic acid isopropyl ester, 4-vinyl benzoic acid 1-(chloromethyl)ethyl ester, 4-vinyl benzoic acid 1-(bromomethyl) ethyl ester, 4-vinyl benzoic acid n-butyl ester, 4-vinyl benzoic acid 4-chlorobutyl ester, 4-vinyl benzoic acid 4-bromobutyl ester, 4-vinyl benzoic acid isobutyl ester, 4-vinyl benzoic acid 3-chloro-1-methylpropyl ester, 4-vinyl benzoic acid 3-bromo-1-methylpropyl ester, 4-vinyl benzoic acid n-pentyl ester, 4-vinyl benzoic acid 5-chloropentyl ester, 4-vinyl benzoic acid 5-bromopentyl ester, 4-vinyl benzoic acid isopentyl ester, 4-vinyl benzoic acid 4-chloro-1-methylbutyl ester, 4-vinyl benzoic acid 4-bromo-1-methylbutyl ester, 4-vinyl benzoic acid epoxyethyl ester, 4-vinyl benzoic acid 2,3-epoxypropyl ester, 4-vinyl benzoic acid 2, 3-epoxybutyl ester, 4-vinyl benzoic acid 2, 3-epoxy-4-chlorobutyl ester, 4-vinyl benzoic acid 2,3-epoxy-4-bromobutyl ester, 4-vinyl benzoic acid 2-hydroxyethyl ester, 4-vinyl benzoic acid 2-hydroxy-2-methylethyl ester, 4-vinyl benzoic acid 2-(2-hydroxyethoxy) ethyl ester, 4-vinyl benzoic acid 2-(2-hydroxypropoxy) ethyl ester, 4-vinyl benzoic acid 2-chloro-2-(2-hydroxyethoxy) ethyl ester, 4-vinyl benzoic acid 2-bromo-2-(2-hydroxy-ethoxy) ethyl ester, 4-vinyl benzoic acid 3,6-dioxo-8-hydroxyoctyl ester, 4-vinyl benzoic acid 3,6-dioxo-8-hydroxynonyl ester, 4-vinyl benzoic acid 5-chloro 3,6-dioxo-8-hydroxyoctyl ester, 4-vinyl benzoic acid 5-bromo 3,6-dioxo-8-hydroxy-octyl ester, 4-vinyl benzoic acid 3,6,9-trioxo-11-hydroxyundecyl ester, 4-vinyl benzoic acid 3,6,9-trioxo-11-hydroxydodecyl ester, 4-vinyl benzoic acid 8-chloro-11-hydroxy-3,6,9-trioxoundecyl ester, 4-vinyl benzoic acid 8-bromo-11-hydroxy-3,6,9-trioxoundecyl ester etc. While, in case of $R_1$=CH$_3$, 4-allyl benzoic acids are listed as material examples. The acids are with 4-allyl groups altered from 4-vinyl groups of the above 4-vinyl benzoic acid and esters. These can be used individually or in combination. For example, 4-vinyl benzoic acid or 4-allyl benzoic acid can be used together with other compounds of the general formula (I).

(B) vinyl compounds used together with compounds shown by (A) general formula (I) are polyethylene glycol dimethacrylate and the like, 2-hydroxy ethyl methacrylate, tetrahydro furfuryl methacrylate, 2, 2-bis [4-(2-methacryloxyethoxy) phenyl) propane, acrylo nitril, vinyl acetate, 2-cyano-acryl acid ester, styrene, divinylbenzene etc. They are used alone or in combination. The combination of triethylene glycol dimethacrylate and 2, 2-bis [4-(2-methacryloxyethoxy) phenyl) is preferably used.

Also followings are enumerated as a kind of vinyl compound known under the name of so-called silane coupling agent, i. e. vinyltrichlorsilane, vinyltrimethoxysilane, vinyltriethoxysilane, vinyltris (2-methoxyethoxy) silane, vinyltriacetoxysilane, allyltrimethoxysilane, allyltriethoxysilane, γ-methacryloxy-propyltrimethoxysilane etc. and these are used individually or in combination. The combination of γ-methacryloxypropyltrimethoxysilane and vinyltrimethoxysilane is preferably used.

As silane compounds followings are enumerated other than those listed above. They are γ-chloropropyltrimethoxysilane, γ-aminopropyltrimethoxysilane, γ-(2-aminoethyl) aminopropyltrimethoxysilane, γ-mercaptopropyltrimethoxysilane, γ-glycidoxypropyltrimethoxysilane, γ-glycidoxypropyldimethylethoxysilane, (γ-glycidoxypropyl) methyldiethoxysilane, β-(3, 4-epoxycyclohexyl) ethyltrimethoxysilane, chloromethyl-triethoxysilane, chloromethyldiethoxysilane etc.

As for the ratio of the compounds shown by (A) general formula (I) of the present invention and (B) vinyl compounds, it is desirable that the compound shown by (A) general formual (I) occupies 0.1 to 10 weight percent of the total weight of (A) and (B) compounds.

As (C) free radical generator to be used, there are all kinds of peroxides such as benzoylperoxide and dicumyl peroxide and azobisisobutyronitril. When polymerization and adhesion is conducted at room temperature, redox-polymerization catalyst which is the combination of all kinds of peroxides as benzoylperoxide and aromatic tertiary amines such as N,N-dimethyl-p-toluidine and N,N-diethanol-p-toluidine are used and particularly, benzoylperoxide-N,N-diethanol-p-toluidine is desirable to be used.

Further, when polymerization and adhesion is conducted under the application of ultra-violet rays, there are benzoinmethyl ether, benzoinethyl ether, benzoinisopropyl ether as (C) light intensifier. While under the application of visible ray, camphoroquinone-N,N-dimethylaminoethylmethacrylate is desirable to be used.

When free radical developing agent and intensifier are contained in composites, it is not necessary to use composite resin. Due to their characteristic polymerization and hardening these composites are possible to be applied to practical treatment, for example, as fillers for small cavities and grooves or a meterial to shut off the external stimulus when the tartar is removed.

The amount of (C) to be used is approx. 0.1 to 5 weight percent of the total weight of compounds shown by (A) general formula (I) and all kinds of vinyl compounds of (B).

Followings are the summary of the composition range of the composites, (A), (B) and (C) of the present invention. Generally, the range is (A) 0.1-10 weight percent, (B) 85-99 weight percent (organic silane compound 0.1-2 weight percent), (C) 0.1-5 weight percent, but a desirable range is weight percent (organic (A) 2-5 weight percent, (B) 92-96 silane compound 0.5-1.5 weight percent), (C) 0.1-5 weight percent.

According to the present invention, composites which do not contain (C) free radical developing agents and/or light intensifier can be used in combination with other composites containing free radical developing agents and/or light intensifier.

The composites of the present invention, particularly adhesive composites, anti-irritation and anti-harmfulness composites against tissue, pulp and the like, can further be combined with other additon agents, for example, inorganic powdered fillers such as kaolin, talc, clay, silica, alumina and glass, and others such as adhesion providing agent, polymerization accelerating agent, polymerization controlling agent and polymerization restraining agent. Wax, ethylenevinyl acetate copolymer will come under the category of adhesion providing agent. In case of adhesive composites polymethylmethacrylate, polyethylmethacrylate etc., will also come uder this category and yet these polymethylmethacrylate and polyethylmethacrylate can be used as bone material same as inorganic powdered fillers. A free radical developing agent is applicable to polymerization accelerating agent and nitro compounds such as nitrobenzene to polymerization controlling agent. As polymerization restraining agent, the following are enumerated such as hydroquinone, hydroquinone monomethylether, butyrated hydroxytoluene, 2-hydroxy-3-methoxy benzophenon and etc.

The bonding agent of the present invention generally does not require solvent and it is desirable to be used by dissolving the compounds (A) shown general formula (I) into vinyl compounds (B) evenly. However, the following methods can also be adopted, that is, a method of dissolving (A) the compounds shown by general formula (I), (B) vinyl compounds and (C) adhesive composites containing free radical developing agents and/or light intensifier into solvent such as alcohol and ketone, applying the solution to the material to be adhered and letting the solvent evaporate for hardening and adhesion, or another of dissolving adhesive composites containing (A) compounds shown by general formula (I) and (B) vinyl compounds into solvent such as alcohol and ketone, applying the solution to the material to be adhered and letting the solvent evaporate. And then, other adhesive composites containing (C) free radical developing agent and/or light intensifier are applied or heaped up for copolymerization adhesion.

Followings are desirable practice methods; for example, a method of mixing (A) compounds shown by general formula (I) with (B) methylmethacrylate and polymethylmethacrylate at normal temperature in the presence of (C) benzoylperoxide-N,N-diethanol-p-toluidine to build an adhesive layer, similarly, another method of mixing (A) compounds shown general formula (I) with (B) 2,2-bis[4-(2-methacryloxyethoxy) phenyl]propane, triethylene glycol dimethacrylate and silica at normal temperature in the presence of (C) benzoylperoxide-N, N-diethanol-p-toluidine to build an adhesive layer and other method of mixing (A) compounds shown by general formula (I) with (B) 2, 2-bis [4-(2-methacryloxy)- phenyl]propane, triethylene glycol dimethacrylate and alcohol at normal temperature and heaping up a dental material such as so called composite resin for copolymerization adhesion after evaporation of alcohol.

Besides, it is desirable that the anti-irritation and anti-harmfulness compounds against tissue, pulp and the like, of the present invention are used to cover a tooth when its dentin is exposed to show some hyperesthesia in the following manner, that is, dissolving adhesive composites containing (A) compounds shown by general formula (I) and (B) vinyl compounds into solvent such as alcohol and ketone, applying the solution to the material to be adhered, letting the solvent evaporate and applying or heaping up other composites containing (C) free radical developing agents and/or light intensifier for copolymerization adhesion, or dissolving (A) compounds shown by general formula (I), (B) vinyl compounds and (C) composites containing free radical developing agents and/or light intensifier into solvent such as alcohol and ketone, applying the solution to the material to be adhered and letting the solvent evaporate for hardening and adhesion.

As practice methods, followings are desirable; for example, a method of mixing (A) compounds shown by general formula (I) with (B) 2, 2-bis [4-(2-methacryloxyethoxy)phenyl]propane, triethylene glycol dimethacrylate and alcohol at normal temperature and heaping up a dental material such as so-called composite resin for copolymerization adhesion after evaporation of alcohol and another method of mixing (A) compounds shown by general formula (I) with (B) 2,2-bis [4-(2-methacryloxyethoxy) phenol]propane, triethyleneglycol dimethacrylate and silica at normal temperature in the presence of (C) benzoylperoxide-N,N-diethanol-p-toluidine to build an adhesive layer.

The composites of the present invention are preferably applied to teeth in the following cases; to the teeth which sense to cold water with slight hyperesthesia, palpation and brushing with hyperesthesia, cold water and palpation with $C_2$, cold water with hyperesthesia under the condition diagnosed as simple pulpitis, and to other parts of teeth, a mere cavity of enamel which does not show any particular unpleasant symptom before treatment, all parts of caries including other initial caries, and part of cervix dentis affected by periodontal desease The composites of the present invention have not only excellent adhesiveness to dentin but anti-irritation and anti-harmfulness against tissue, pulp and the like.

And the bonding agent containing (A) compounds shown by general formula (I) and (B) vinyl compounds is excellent in adhesiveness, particularly in water-resistance and durability, and it can be used for various purposes. Above all, it is ideal for teeth, metal, ceramics and the undercoating of paints.

As previously mentioned, methylmethacrylate polymer and copolymer of vinyl compounds such as 2,2-bis[4-(2-methacryloxyethoxy) phenyl]propane and triethylene glycol dimethacrylate have been known as bonding agents for teeth, but due to their insufficient adhesive force against teeth they were used after teeth had been treated with strong acid.

On the contrary, the bonding agent of the present invention comprising (A) compounds shown by general formula (I) and (B) vinyl compounds has so strong an adhesive force that conventional treatment with strong acid is not necessarily required. Therefore, the present invention is invaluable from the standpoint of labor-saving in dental treatment and protecting teeth from damaging their surface by dissolving it with acid more than necessary. Also it has been pointed out that though there are some bonding agents with similar function to that of the present invention as previously mentioned, a restriction is imposed on its polymerization manner and moreover, the polymerization speed is slow or they leave a lot of un-polymerization parts. The present invention, in case of polymerization at normal temperature, is considerably advantageous to adhesion because the simplest catalyst, redox-polymerization catalyst such as benzoylperoxide-N,N-diethanol-p-toluidine can be used, the polymerization speed can be controlled to the desired degree, and yet nonpolymerized portion is limited.

Besides, conventional bonding agents for teeth such as methylmethacrylate polymer and copolymer of vinyl compounds like 2,2bis[4-(2-methacryloxyethoxy)-phenyl]propane and triethylene glycol dimethacrylate do not show sufficient adhesiveness, nor anti-irritation and anti-harmfulness against tissue, pulp and the like, at all, while the composites of the present invention containing (A) the compounds shown by general formula (I) and (B) vinyl compounds are excellent in adhesiveness, particularly in water-resistance and durability. Since they have not only excellent adhesiveness to teeth but anti-irritation and anti-harmfulness against tissue, pulp and the like, they are useful for dental treatment. When these composites are used, the dissolution of the surface of the applicable teeth is limited because the teeth are not necessarily required to be treated with strong acid. Therefore, the composites of the present invention have a great value for dental treatment.

In addition to the above, the present invention, for example, in case of polymerization at normal temperature, is also outstanding as for adhesiveness because the simplest catalyst, redox-polymerlization catalyst such as benzoylperoxide-N,N-diethanol-p-toluidine can be used and the polymerization speed can be controlled to the desired degree and there is a limited non-polymerized portion.

EXAMPLES

The present invention is explained by practical examples as the following, but the scope of the invention would not be restricted by them.

EXAMPLE 1

Composites consisting of powder and liquid were prepared as a bonding agent and named A Compound.

| A Compound: | |
| --- | --- |
| Powdered Component | Weight |
| Polymethylmethacrylate fine powder | 98.5 |
| Benzoylperoxide | 1.5 |
| Liquid Component | |
| Methylmethacrylate | 97.5 |
| 4-vinyl benzoic acid | 1.5 |
| N,N—diethanol-p-toluidine | 1.0 |

A vinyl tape (10 mm in diamter) with a round hole of 6 mm in diamter was pasted to the front side of a bovine front tooth ater it was well ground and smoothed with No.6/0 emery paper. After A Compound was applied to the hole slightly thick with a little brush by so-called "Brush-on technique", an acrylate bar with 6 mm in diameter was adhered. One hour later the bovine tooth with the acrylate bar adhered was sunk as it was in water at 37° C. 24 hours later the tooth was taken out of water and the adhesive force was measured with automatograph. The adhesive force registered 54.2 kg/cm².

As a comparative example, 1.0 part by weight of N,N-diethanol-p-toluidine was dissolved into 99.0 parts by weight of methylmethacrylate for compounding without containing 1.5 parts by weight of 4-vinyl benzoic acid of liquid component of Example 1, A Compound. The method of Example 1 was repeated with this liquid component in combination with powdered component of A Compound. The adhesive force was 0 kg/cm².

EXAMPLE 2

Composites consisting of powder and liquid same as A Compound of Example 1 were prepared and named B Compound.

| B Compound: | |
| --- | --- |
| Powdered Component | Weight |
| Polymethylmethacrylate fine powder | 98.5 |
| Benzoylperoxide | 1.5 |
| Liquid Component | |
| Methylmethacrylate | 97.5 |
| 4-vinyl benzoic acid ethyl ester | 1.5 |
| N,N—diethanol-p-toluidine | 1.0 |

Example 1 was repeated by using B Compound instead of A Compound of Example 1. The adhesive force registered 43.5 kg/cm².

EXAMPLE 3

Composites consisting of powder and liquid were prepared as a bonding agent and named C Compound.

| C Compound: | |
| --- | --- |
| Powdered Component | Weight |
| Silane treatment silica fine powder* | 98.5 |
| Benzoylperoxide | 1.5 |
| Liquid Component | |
| 2,2-bis [4-(2-methacryloxyethoxy phenyl)propane] | 62.0 |
| Triethyleneglycoldimethacrylate | 35.5 |
| 4-vinyl benzoic acid | 1.5 |
| N,N—diethanol-p-toluidine | 1.0 |

*Silica powder ranging from 35 to 1 micron of granulation degree was treated with solution which was obtained by adjusting 95% ethanol to be pH 4.5–5.5 with acetic acid and adding γ-methacryloxypropyltrimethoxysilane so that the solution would show concentration of 2 weight percent. Slurry of this silica powder was dried up at 120° C. and silane was adhered.

A piece of metal of approx. 10 mm × 10 mm was well ground with No.1 emery paper to make the surface smooth and a vinyl tape (10 mm in diameter) with a round hole of 6 mm in diameter was pasted there. After C Compound was apllied to the round hole slightly thick by "Brush-on technique", a stainless bar of 6 mm in. diamter was adhered. One hour later the metal plate with the stainless bar adhered was sunk as it was in water at 37° C. 24 hours later the metal was taken out of water and the adhesive force was measured with automatograph. The result is shown by Table 1.

As a comparative example, 37.0 parts by weight of triethyleneglycol dimethacrylate and 1.0 part by weight of N,N-diethanol-p-toluidine were dissolved into 62.0 parts by weight of 2,2-bis[4-(2-methacryloxyethoxy)-phenyl]propane for preparing liquid component without containing 1.5 parts by weight of 4-vinyl benzoic acid of liquid component of Example 3, C Compound. The method of Example 3 was repeated with this liquid component in combination with the powdered component of C Compound. The result is shown by Table 1.

TABLE 1

| Pieces of Metal | Adhesive Force (kg/cm²) |
| --- | --- |
| Examples | |
| Coba Chrome | *170.8 and more |
| Nine Star | *157.8 and more |
| Shikenkin 12 Palaa Gold | *154.6 and more |
| Palla Gold | *161.3 and more |
| Stainless Steel(SUS-304) | 120.5 |
| Comparison | |
| Coba Chrome | 23.6 |

TABLE 1-continued

| Pieces of Metal | Adhesive Force (kg/cm²) |
|---|---|
| Nine Star | 19.1 |

The composition of metal of the table are as follows:
Coba Chrome: Cobalt Chrome alloy for dental casting
Nine Star: Nickel Chrome alloy for dental casting
Shikenkin 12 Palla Gold: Gold-Palladium alloy for dental casting
Palla Gold: Silver-Palladium alloy for dental casting
All are products of Nippon Shiken Kogyo, Japan
*: The layers of the bonding agents were brokon by measuring adhesive force.

EXAMPLE 4

After a piece of metal with a stainless bar adhered was sunk in water at 37° C. for 24 hours according to the method of Example 3, it was sunk in water at 4° C. and 60° C. for one minute in turn each time totaling 60 times for 2 hours and the adhesive force was measured. The result is shown by Table 2.

As a comparative example, the method of Example 4 was repeated by using same stuffs adopted by the comparative example of Example 3. The result is shown by Table 2.

TABLE 2

| Pieces of Metal | Adhesive Force (kg/cm²) |
|---|---|
| Examples | |
| Coba Chrome | *149.1 and more |
| Nine Star | *122.2 and more |
| Shikenkin 12 Palla Gold | *147.8 and more |
| Palla Gold | *136.1 and more |
| Stainless Steel (SUS-304) | 100.1 |
| Comparison | |
| Coba Chrome | 20.9 |
| Nine Star | 13.8 |

*: The layers of the bonding agents were broken by measuring adhesive force.

EXAMPLE 5

The bottom of a cylindrical ceramic material of 10 mm in diameter and 8 mm in height (commodity name: VITAVMK "68" by VITA) which was baked for dental use was well ground for flat and smooth surface, and a vinyl tape (10 mm in diameter) with a round hole of 6 mm in diameter was pasted to the bottom. After C Compound was applied to the hole slightly thick by "Brush-on technique", a stainless bar of 6 mm in diameter was adhered. One hour later the ceramic material with the stainless bar adhered was sunk in water at 37° C. 24 hours later the material was taken out of water and measured with autometograph. The adhesive layer was broken when the adhesive power registered 50.3 kg/cm².

As a comparative example, the method of Example 5 was repeated by using same stuffs adopted by the comparative example of Example 3. The adhesive force registered 1.8 kg/cm².

EXAMPLE 6

Liquid composites were prepared as an application compound and named D Compound.

| D Compound: | |
|---|---|
| | Weight |
| 2,2-bis[4-(2-methacryloxyethoxy)propane | 30.0 |
| Triethyleneglycoldimethacrylate | 18.0 |
| 4-vinyl benzoic acid | 2.0 |
| Ethyl alcohol | 50.0 |

As fillers, two types of pastes comprising vinyl compounds, inorganic filler and polymerization initiator respectively were prepared, and named $P_1$ Paste and $P_2$ Paste respectively.

They are mixed to P Paste.

| $P_1$ Paste: | |
|---|---|
| 2,2-bis[4-(2-methacryloxyethoxy)phenyl]propane | 21.0 |
| Triethyleneglycoldimethacrylate | 6.0 |
| Silane treatment silica powder* | 71.0 |
| N,N—diethanol-p-toluidine | 2.0 |
| $P_2$ Paste: | |
| 2,2-bis[4-(2-methacryloxyethoxy)phenyl]propane | 21.0 |
| Triethyleneglycoldimethacrylate | 6.0 |
| Silane treatment silica powder | 71.5 |
| Benzoylperoxide | 1.5 |

*Same silica powder adopted by C Compound of Example 3 was used.

Using the molar of a newly pulled out human tooth, a cavity of 4 mmφ in diameter and 3 mm in depth was formed on its cervix with the air turbine and was completely dried with air after the enamel substance was treated with aqueous solution of 40% phosphoric acid and then thoroughly rinsed. Then, after D Compound was thinly applied to the cavity wall and solvent was blown off with air, P Paste was filled in the cavity. It took about three minutes for hardening. This was sunk in fuchsin solution at 4° C. and 60° C. for one minute in turn each time totaling 60 times for 2 hours and the progress of permeation of coloring matter was observed to evaluate the effectuality of brim blocking. The observation verified that permeation was not recognized at all and its effectuality of blocking was excellent.

As a comparative example, 20.0 parts by weight of triethyleneglycoldimethacrylate and 50.0 parts by weight of ethylalcohol were dissolved into 30.0 parts by weight of 2,2-bis[4-(2-methacryloxyethoxy)phenyl]propane for liquid composites without containing 1.5 parts by weight of vinyl benzoic acid of the composite of D Compound of Example 6. The method of Example 6 was repeated with this compound instead of D Compound of Example 6. The result was that the permeation of coloring matter was observed at various spots and the brim blocking was not effective.

EXAMPLE 7

Liquid composite was prepared as an application compound and named A Compound.

| A Compound: | |
|---|---|
| | Weight % |
| Triethyleneglycoldimethacrylate | 47.0 |
| 4-vinyl benzoic acid | 2.0 |
| Methacryloxypropyltrimethoxysilane | 1.0 |
| Ethyl alcohol | 50.0 |

As fillers, two types of pastes comprising vinyl compounds, inorganic filler and polymerization initiator respectively were prepared and named $P_1$ Paste and $P_2$ Paste respectively. They are mixed to P paste.

| $P_1$ Paste: | |
|---|---|
| 2,2-bis[4-(2-methacryloxyethoxy)phenyl]propane | 21.0 |
| Triethyleneglycoldimethacrylate | 6.0 |
| Silane treatment silica powder | 71.0 |
| N N—diethanol-p-toluidine | 2.0 |
| $P_2$ Paste: | |
| 2,2-bis[4-(2-methacryloxyethoxy)phenyl]propane | 21.0 |

-continued

| | |
|---|---|
| Triethyleneglycoldimethacrylate | 6.0 |
| Silane treatment silica powder* | 71.5 |
| Benzoylperoxide | 1.5 |

*Silica powder ranging from 35 to 1 micron of granulation degree was treated with solution which was obtained by adjusting 95% ethanol to be pH 4.5–5.5 with acetic acid and adding γ-methacryloxypropyltrimethoxysilane so that the solution would show concentration of 2 weight percent.

Fifth grade cavity was formed on a grown up dog's tooth which was considered healthy by injecting water with the air turbine. Then, after A Compound was thinly applied to the cavity wall and the solvent was blown off with air, P Paste was filled in the cavity. Prior to the experiment a venos injection of sodium pentobalbital had been given to the experimental animal for anesthesia. It took about three minutes for hardening. The experimental animal was killed 14 days after the experiment. After the experimental tooth was fixed in 10% formalin, it was delimed. The tooth was buried in celloidine to be cut into consecutive fragments and colored with a mixture of hematoxylin and eosin to examine with a microscope. The result was that no serious change was observed according to a medical opinion and the medical check record was excellent.

As a comparative example, P Paste alone was filled in a tooth opposite to the one used in Example 1 without using A Compound of Example 1 and the method of Example 1 was repeated. The result was that a remarkable change was observed according to a medical opinion and the medical check record was poor.

EXAMPLE 8

Liquid composites consisting of two types of solution were prepared as an application compound and named $B_1$ compound and $B_2$ compound. They are mixed to B Compound.

| | Weight % |
|---|---|
| $B_1$ Compound: | |
| Triethyleneglycoldimethacrylate | 95.5 |
| 4-vinyl benzoic acid | 2.0 |
| γ-methacryloxypropyltrimethoxysilane | 1.0 |
| Benzoylperoxide | 1.5 |
| $B_2$ Compound: | |
| N,N—diethanol-p-toluidine | 1.0 |
| Ethyl alcohol | 99.0 |

P Paste was prepared same as Example 7.

Experiment was conducted same as Example 1 except that fifth grade cavity was formed on a grown up dog's tooth which was considered healthy by injecting water with the air turbine and P Paste was filled in the cavity after B Compound, a mixture of $B_1$ compound and $B_2$ compound was thinly applied to the cavity wall and the solvent was blown off. It took about three minutes for hardening. The result was that no serious change was observed according to a medical opinion and the medical check record was excellent.

As a comparative example, P Paste alone was filled in a tooth opposite to the one used in Example 8 without using B Compound of Example 8. The result was that a remarkable change was observed according to a medical opinion and the medical check record was poor.

EXAMPLE 9

A Compound and P Paste same as Example 7 were prepared.

Fifth grade cavity was formed with the air turbine on the right 3rd tooth of human upper jaw, which was regarded as simple pulpitis to show hyperesthesia against cold water (diagnosis $C_2$ Simple pul). After the inside of the cavity was washed with water and dried, the brim of the cavity was treated with acid treatment solution (40% phosphoric acid solution) and again washed with water and dried. Then A Compound was thinly applied to the cavity wall and the solvent was blown off with air. The patient was requested to visit the dentist during the treatment period to examine the condition of the part of tooth being repaired and presence of clinical symptom. The result showed that all of these symptoms disappeared within three days of treatment.

As for this case of symptom, heretofore, such cavity was normally capped with a material made of calcium hydroxide and the like, at an early stage. Because in many cases the clinical symptom either remained as it was or diteriorated, and mitigation or extinction of the clinical symptom was not known when the cavity was not capped.

EXAMPLE 10

B Compound and P Paste same as Example 8 were used and a clinical experiment same as Example 9 was conducted.

The result showed that the symptom of hyperesthesia disappeared within three days of treatment and the repaired part of the tooth showed an excellent condition.

EXAMPLE 11

Liquid composite was prepared as an application compound and named C Compound.

| C Compound: | Weight % |
|---|---|
| 2,2-bis[4-(2-methacryloxyethoxy)phenyl]propane | 20.0 |
| Triethyleneglycoldimethacrylate | 27.0 |
| 4-vinyl benzoic acid | 2.0 |
| γ-methacryloxypropyl-trimethoxysilane | 1.0 |
| Ethyl alcohol | 50.0 |

An experimental pathological test and clinical test same as Example 7 and 9 were conducted by using this C Compound and P Paste.

The result was that no serious change was observed according to a medical opinion and the medical check record was excellent same as Example 7.

While, concerning the clinical test, the symptom of hyperesthesia disappeared within three days of treatment and the repaired part of the tooth showed an excellent condition.

EXAMPLE 12

Liquid composite consisting of two types of solution was prepared as an application compound and named $D_1$ compound and $D_2$ compound respectively. They are mixed to be called D Compound.

| | Weight % |
|---|---|
| $P_1$ Compound: | |
| 2,2-bis[4-(2-methacryloxyethoxy)phenyl]propane | 40.5 |
| Triethyleneglycoldimethacrylate | 55.0 |
| 4-vinyl benzoic acid | 2.0 |
| γ-methacryloxypropyltrimethoxysilane | 1.0 |

| Composite | Weight % |
| --- | --- |
| Benzoylperoxide | 1.5 |
| D₂ Compound: | |
| N,N—diethanol-p-toluidine | 1.0 |
| Ethyl alcohol | 99.0 |

An experimental pathological test and a clinical test same as Example 7 and 9 were conducted by using this D Compound and P Paste.

The result was that no serious change was observed according to a medical opinion and the medical check record was excellent same as Example 7.

While, concerning the clinical test, the symptom of hyperesthesia disappeared within three days of treatment and the repaired part of the tooth showed an excellent condition.

EXAMPLE 13

Each of the following composite was prepared.

| Composite | Weight % |
| --- | --- |
| E Compound (single solution type) | |
| Triethyleneglycoldimethacrylate | 48.0 |
| 4-vinyl benzoic acid | 2.0 |
| Ethyl alcohol | 50.0 |
| F Compound (double solution type) | |
| F₁ Compound: | |
| Triethyleneglycoldimethacrylate | 96.5 |
| 4-vinyl benzoic acid | 2.0 |
| Benzoylperoxide | 1.5 |
| F₂ Compound: | |
| N,N—diethanol-p-toluidine | 1.0 |
| Ethyl alcohol | 99.0 |
| G Compound (single solution type) | |
| 2,2-bis[4-(2-methacryloxyethoxy)phenyl]propane | 20.0 |
| Triethyleneglycoldimethacrylate | 28.0 |
| 4-vinyl benzoic acid | 2.0 |
| Ethyl alcohol | 50.0 |
| H Compound (double solution type) | |
| H₁ Compound: | |
| 2,2-bis[4-(2-methacryloxyethoxy)phenyl]propane | 41.0 |
| Triethyleneglycoldimethacrylate | 55.0 |
| 4-vinyl benzoic acid | 2.0 |
| Benzoylperoxide | 1.5 |
| H₂ Compound: | |
| N,N—diethanol-p-toluidine | 1.0 |
| Ethyl alcohol | 99.0 |

As the result of conducting an experimental pathological test and a clinical test in the same manner as Example 7 and 9 by using each compound and P Paste, a similar result was obtained.

EXAMPLE 14

Each of the following composite was compounded.

| Composite | Weight % |
| --- | --- |
| I Compound (single solution type) | |
| Triethyleneglycoldimethacrylate | 47.0 |
| 4-vinyl benzoic acid | 2.0 |
| γ-glycidoxypropyltrimethoxysilane | 1.0 |
| Ethyl alcohol | 50.0 |
| J Compound (double solution type) | |
| J₁ Compound: | |
| Triethyleneglycoldimethacrylate | 95.5 |
| 4-vinyl benzoic acid | 2.0 |
| γ-glycidoxypropyltrimethoxysilane | 1.0 |
| Benzoylperoxide | 1.5 |

| Composite | Weight % |
| --- | --- |
| J₂ Compound: | |
| N,N—diethanol-p-toluidine | 1.0 |
| Ethyl alcohol | 99.0 |
| K Compound (single solution type) | |
| 2,2-bis[4-(2-methacryloxyethoxy)phenyl]propane | 20.0 |
| Triethyleneglycoldimethacrylate | 27.0 |
| 4-vinyl benzoic acid | 2.0 |
| γ-glycidoxypropyltrimethoxysilane | 1.0 |
| Ethyl alcohol | 50.0 |
| L Compound (double solution type) | |
| L₁ Compound: | |
| 2,2-bis[4-(2-methacryloxyethoxy)phenyl]propane | 40.5 |
| Triethyleneglycoldimethacrylate | 55.0 |
| 4-vinyl benzoic acid | 2.0 |
| γ-glycidoxypropyltrimethoxysilane | 1.0 |
| Benzoylperoxide | 1.5 |
| L₂ Compound: | |
| N,N—diethanol-p-toluidine | 1.0 |
| Ethyl alcohol | 99.0 |

As the result of conducting an experimental pathological test and a clinical test in the same manner as Example 7 and 9 by using each compound and P Paste, a similar result was obtained.

What is claimed is:

1. A dental bonding composition consisting essentially of:

(A) Compounds of general formula

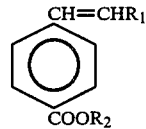

wherein $R_1$ comprises hydrogen or a methyl group and $R_2$ comprises hydrogen, an alkyl group with 1–5 carbon atoms which may be substituted with halogen, an alkyleneoxide group with 2–4 carbon atoms which may be substituted with halogen, or an $-(CH_2CH_2O)_nH$ group wherein n is an integer of from 1–4 wherein the carbon atoms may be substituted with eighter halogen or a methyl group; and (B) a vinyl compound selected from the group consisting of methylmethacrylate ester, polyethylene glycol dimethacrylate, 2-hydroxy ethyl methacrylate, tetrahydro furfuryl methacrylate, 2,2-bis[4-(2-methacryloxyethoxy)phenyl]propane, acrylonitril, vinyl acetate, 2-cyano acryl acid ester, styrene, divinylbenzene, and mixtures thereof.

2. Composition according to claim 1, further containing a silane compound.

3. Composition according to claim 1 wherein (A) is a compound selected from the group consisting of 4-vinyl benzoic acid, 4-vinyl benzoic acid ester, 4-allyl benzoic acid and 4-allyl benzoic acid ester.

4. Composition according to claim 3, further containing a silane compound.

5. Composition according to claim 1 wherein the vinyl compound is selected from the group consisting of methylmethacrylate, triethyleneglycol-dimethacrylate and 2,2-bis[4-(2-methacryloxyethoxy) phenyl]-propane.

6. Composition according to claim 5, further containing a silane compound.

7. Composition according to claim 2 wherein silane compound is silane coupling agent.

8. Composition according to claim 7 wherein said silane coupling agent is a compound selected from the group consisting of γ-methacryloxypropyltrimethoxysilane and γ-glycydoxypropyl-trimethoxy silane.

9. Composition according to claim 1 further containing a free radical developing agent which comprises a redox-polymerization catalyst.

10. Composition according to claim 9 wherein the redox-polymerization catalyst comprises benzoylperoxide and N,N-diethanol-p-toluidine.

11. Composition according to claim 9, further containing a silane compound.

12. Composition according to claim 11 wherein said redox-polymerization catalyst comprises benzoylperoxide and N,N-diethanol-p-toluidine.

13. Composition according to claim 1 further containing a light sensitizer comprising a compound selected from the group consisting of benzoinether and camphoroquinone-N,N-dimethyl-aminoethyl-methacrylate.

14. Composition according to claim 13, further containing a silane compound.

15. Composition according to claim 1 further containing inorganic fillers.

16. Composition according to claim 15 wherein said inorganic filler is silica.

17. Composition according to claim 2, further containing inorganic fillers.

18. Composition according to claim 17, wherein said inorganic filler is silica.

19. Composition according to claim 1 further containing an adhesion promoting agent.

20. Composition according to claim 19 wherein said adhesion promoting agent is polymethylmethacrylate.

21. Composition according to claim 2, further containing an adhesion promoting agent.

22. Composition according to claim 21 wherein said adhesion promoting agent is polymethylmethacrylate.

* * * * *